(12) United States Patent
Walker et al.

(10) Patent No.: US 6,767,919 B2
(45) Date of Patent: Jul. 27, 2004

(54) HIGH SPECIFICITY ANTICANCER AGENTS

(75) Inventors: Evan Harris Walker, Aberdeen, MD (US); Eduardo Palomino, Royal Oak, MI (US); Steven L. Blumenthal, Boynton Beach, FL (US)

(73) Assignee: Walker Cancer Research Institute, Inc., Aberdeen, MD (US)

( * ) Notice: Subject to any disclaimer, the term of this patent is extended or adjusted under 35 U.S.C. 154(b) by 0 days.

(21) Appl. No.: 10/321,304

(22) Filed: Dec. 17, 2002

(65) Prior Publication Data

US 2004/0116508 A1 Jun. 17, 2004

(51) Int. Cl.$^7$ ............... A61K 31/38; C07D 327/00; C07D 335/08
(52) U.S. Cl. ............... 514/437; 549/4; 549/27
(58) Field of Search ............... 514/437; 549/4, 549/27

(56) References Cited

U.S. PATENT DOCUMENTS

| | | | | |
|---|---|---|---|---|
| 6,025,408 A | * | 2/2000 | Williams et al. | 522/53 |
| 6,100,253 A | * | 8/2000 | Andersen et al. | 514/211.1 |
| 6,117,869 A | * | 9/2000 | Picard et al. | 514/227.5 |
| 6,391,911 B1 | * | 5/2002 | Bases | 514/437 |
| 6,693,136 B1 | * | 2/2004 | Lee et al. | 514/603 |

* cited by examiner

*Primary Examiner*—Deborah C. Lambkin
(74) *Attorney, Agent, or Firm*—Frommer Lawrence & Haug LLP; William S. Frommer; Sandra Kuzmich

(57) ABSTRACT

A process for producing new anticancer drugs such that the drugs can be administered in a nontoxic, proto-drug form and, subsequent to a time delay which allows for differential concentration in the target cancer or invasive tissues or cells, the non-toxic drug is then modified by an activation drug to selectively provide toxic levels of a pharmacologically active agent to the target issue.

23 Claims, No Drawings

HIGH SPECIFICITY ANTICANCER AGENTS

BACKGROUND OF THE INVENTION

Despite advances in the discovery of antitumor agents, cancer remains a disease with very poor prognosis. Substances displaying in vitro and in vivo anticancer activity are continuously reported in the literature, but only a scant number of those substances go past a phase II clinical trial. Moreover, the cure rates of drugs for the treatment of cancers are unacceptably low, and the side effects of these drugs are severe. The toxic effects of the drugs on the cancer tissues only marginally exceed their toxic effects on normal, healthy cells of the body that should be protected from the effects of the drugs. Moreover, that high failure rate of potential anticancer agents arguably can be traced to the lack of methods to ascertain and to design into, in advance, control of secondary effects, specificity, and high target-tissue activity in human subjects. A design process is needed to design into candidate compounds all the requirements for the drug delivery system and anticancer effectiveness. That goal is achieved by the present invention.

Chemotherapy research in cancer treatment has been largely devoted to the search for drugs providing toxin specificity to destroy neoplastic tissue in the body without exceeding toxic exposure levels injurious to healthy tissues, that is to say, to the search for cytotoxic drugs that concentrate in neoplastic tissues, or for drugs that metabolize into such toxins. Although major efforts to this end have been made, success has been achieved for only a few cancer types. For most cancer types, success has been quite limited.

Modern anticancer drug development began with the recognition that some poison gas exposures in WWI actually had anticancer side effects. The process of anticancer drug development began at this point with the mostly random procedure of searching through known toxins to determine through exposure if the given toxin had differential toxicity that would aid in the control or cure of cancer. The approach centered on the discovery of "single moiety" compounds.

In the 1930s, more complex compounds were developed so designed as to divide the function of the anticancer agent into two parts, or two moieties on the same compound, wherein one moiety would serve to concentrate the drug in the cancer cell or tissue and the second moiety would serve to destroy the cancer cells wherein the compound concentrated. A fundamental advance in this area was the elucidation of chemical entities with tumor tissue selectivity. Early reports on such selectivity were made for the dye Nile blue by Lewis, et al. in *Cancer Res.* 9:736, 1949, a report that prompted the modification of this benzophenoxazine to incorporate a toxin such as a nitrogen mustard as an integral part of the molecule (Sen, et al. in Int. *Union against Cancer Acta*, 26, 774 (1960)). Those attempts at modification of a tumor tissue selective agent with a toxic moiety met with limited success. It has been presumed that the failure of such approaches is due to intrinsic modification of the tissue selectivity of the parent compound with the addition of the toxic moiety. The cause of the failure, however, is more fundamental and is shared by other drug delivery concepts, in particular, the concept of anticancer prodrugs.

Beginning in the early 1950s, the two-moiety drug design approach of a concentrating moiety and a toxic moiety was modified to the two-moiety "prodrug" design, wherein one moiety served to modify or "mask" or "cap" the toxicity of the second toxic moiety of the drug compound until the drug entered the cancer cells. At this point, a chemical reaction, generally intended to be with enzymes specific to the cancer cells, would remove the mask or cap moiety so that the toxic moiety would kill the cancer cells. Again, the prodrug anticancer delivery concept has had limited success.

Both the concept of drugs that combine a concentrating moiety together with a toxic moiety and the concept of prodrugs that are to be metabolized preferentially in cancer tissues suffer from the problems that arise out of the nature of cancer itself: cancer cells and tissues are not foreign biological organisms having a chemistry distinct from normal tissue. These tissues are, in the case of human cancers, human tissues. The normal and neoplastic tissue have essentially the same chemistry; that is, for the most part, both consist of the same chemical molecules and in similar concentrations.

In 1980, Evan Harris Walker in *Perspectives in Biology and Medicine, Spring Issue*, 424–438, (1980) argued that the prodrug concept and the combination of toxin with concentrator concept fail because of the fundamentals of the pharmacokinetics of drug delivery. The time course of the drugs depends on their metabolic uptake and elimination rates. If the rates are lower for the cancer cells than for the normal cells, the drugs will appear to concentrate. That is to say, after a sufficient lapse of time, the drugs will have been metabolized and eliminated out of the normal tissues while still being in significant concentrations in the cancer cells and tissues. This will be the case even though the total amount of drug delivered to both normal and cancer cells may be essentially the same. The problem of achieving an effective anticancer drug was not one of achieving differential concentration, or of having the drug be activated by enzymes in the cells, but rather one of being able to suppress the toxicity of the drug in the normal cells and tissues until the differential concentration of the drug had become favorable.

In order to take advantage of the drug concentration differential between normal and cancer tissue, Walker in *Perspectives in Biology and Medicine, Spring Issue*, 424–438, (1980) proposed a design procedure consisting of two drugs, a prodrug and an "activation" drug. Both the prodrug (that had a design limited to a toxin plus a cap or mask moiety) and the activation drug were to be designed so as to have little or no toxic or other effect on the body (i.e., to be substantially biologically inert) if administered alone. However, in combination, these two compounds would react in the body to produce a compound toxic to the cells wherein it was produced. These two drugs were to be administered sequentially with a time delay between their introduction to allow for the normal cells to metabolize and eliminate the prodrug out of the body before the activation drug was administered. At that point in time—after a time delay for differential delivery of the drug—differential concentration of the prodrug would have been achieved. Removing the masking or capping moiety of the prodrug at that time— when the prodrug would be differentially concentrated in the cancer tissues—would then result in delivery of high levels of the included anticancer toxin. In this way, anticancer toxins would be delivered to cancer cells and tissues without harm being done to normal cells and tissues.

Prodrugs of the type proposed by Walker were designed and synthesized by the present inventors. One of these was a 5-fluorouracil-N-glucoside, which can be activated by the enzyme β-glucosidase. After designing a prodrug of this type, the inventors of the present disclosure found that a more complex prodrug and activation drug system would be needed to provide all the requirements for a selective and effective anticancer pharmaceutical. In particular, the present inventors found that the prodrug and activation design of this type also had limitations in that the differential concentration achievable within the limits of that design was not sufficiently high. In other words, the differential concentration effect due entirely to differential diffusion with no added moiety to enhance the concentration differential proved to be inadequate. A more complex drug system was needed and it was found that a process for the development of the drug system would be required.

SUMMARY OF THE INVENTION

The present disclosure covers an assemblage containing chemicals and chemical moieties, a process for the detailed design of an assemblage, products or devices needed to carry out and evaluate the process, chemical systems designed by the process that serve as specific assemblage examples, and procedures needed for the successful use of an assemblage and the specific examples of assemblages designed by the process disclosed herein.

The assemblage covered by the present disclosure is herein defined as a complex proto-drug and activation drug system. The proto-drug includes one or more differentially selective moieties, one or more toxic moieties, and one or more moieties that serve the purpose of providing a "mask" or "cap" to the toxic moieties.

The present disclosure also covers an activation drug, herein defined as one or more chemicals serving the function of activating the proto-drug of the assemblage. The activation drug removes the mask or cap moiety, or a sufficiency of the mask or cap, or so modifies the chemistry of the overall proto-drug molecule as to substantially eliminate the masking or capping function of the mask or cap, thereby making the resulting compound a toxic, pharmacologically active agent. In addition, the present disclosure covers the introduction of "links" that serve the purpose of chemically tying the moieties of the proto-drug together so as to form a single compound, that alone is substantially biologically inert. The links may be the chemical bonds between the linked moieties or a combination of atom(s) and bonds that connect the moieties of the proto-drug.

The present disclosure also covers a process whereby the proto-drug and activation drug system (i.e., the assemblage) is to be designed and specified. That is to say, the likelihood that such a complex system of chemicals having the set of required properties could be obtained through chance experimentation alone is nil. As a result, it is necessary to develop a process whereby such chemical systems can be produced.

The present disclosure also covers novel products or devices used in the present process.

The present disclosure also covers specific examples of proto-drug and activation drug systems (i.e., assemblages) as produced by the successful use of the process.

DETAILED DESCRIPTION OF THE INVENTION

The assemblage, the process for the detailed design of an assemblage, products or devices needed to carry out and evaluate the process, and procedures needed for the successful use of the examples of the chemical system presently disclosed all serve to provide for a highly selective and effective anticancer pharmaceutical. The examples and corresponding data set forth below serve as specific assemblage examples and demonstrate the successful use of the disclosed process. The process is not limited to the design of an anticancer agent but may also be used to develop other pharmaceuticals where toxicity in a target cell population is required with concomitant low toxic side effects.

An object of the present invention is to provide an assemblage, which assemblage includes a proto-drug and an activation drug, whereby the proto-drug is made of at least one differentially concentrating moiety, at least one toxic moiety and at least one cap moiety. The details of the components of the proto-drug are:

1. The differentially selective moiety or moieties (also referred to as the "differentially concentrating moiety") of a chemical compound having properties such that the compound will differentially concentrate in cancer tissues as compared with normal tissues of the treated body whether in animals or people. Here differentially concentrate means that the ratio of the concentration of the said compound in the cancer tissue as compared to the concentration of that compound in normal tissues will at some time during the pharmacokinetics of the drug become elevated as a result of the difference between absorption, distribution, metabolism, and elimination processes of the drug in the cancer cells as compared to normal cells.

2. The toxic moiety or moieties of a chemical compound having properties such that the compound will be capable of killing the cells or tissues wherein it is concentrated.

3. The mask or cap moiety or moieties of a chemical compound having properties such that the proto-drug's toxicity will not be expressed, that is to say, not act as a toxin in the cell or in the tissue where it is located, until the proto-drug is activated by the application or administration of the activation drug. The term mask or cap moiety is herein defined to be any modification in the proto-drug serving to mollify or eliminate the toxicity of the overall compound whereby such cap is later removed or modified by the activation drug. The term mask or cap need not be, and is not limited to being, a chemical moiety that literally covers, or is chemically bonded directly to the toxic moiety or to the toxic site of the proto-drug.

4. The linkages, meaning chemical bonds or a combination of atoms and bonds between elements of the separate moieties of the proto-rug that include at least one of each of the differentially selective moiety, the toxic moiety, and the cap moiety. Examples of linkages made up of a combination of atoms and bonds include but are not limited to single atoms such as oxygen that can provide a linkage —O— with two bond sites to join two of the required moieties, or groups of different atoms such as an amine (>N—CH$_2$—) that can link three moieties, or an azine (>C:NN:C<) that can link four moieties, if need be, together into a single molecule.

The activation drug of the assemblage is one or more chemical compounds separate from the proto-drug. The activation drug serves the purpose of activating the proto-drug by physical or chemical modification so as to render the resulting compound a toxic, pharmacologically active agent or so as to cause the proto-drug to release a toxic moiety. Both the proto-drug and the activation drug are to be designed so as to have little or no toxic or other effect on the body (i.e., to be substantially biologically inert) if administered alone. However, in combination, the proto-drug and the activation drug will react in the body to produce a compound toxic to the cells wherein such compound is produced.

The fact that the proto-drug and the activation drug are designed so as to have little or no toxic effect on the body when administered alone uniquely distinguishes the disclosed drug design process from previously disclosed methods of drug development. It moves specific elements of the chemical design out of the area of biochemistry and into the predictable discipline of organic chemistry. What has been accomplished by the instant invention is the modification of a conventional prodrug design. Conventional prodrugs depend on the specifics of biochemical reactions within body tissues to be converted into a pharmacologically active compound. The proto-drug of the instant invention is a substantially biologically inert compound that is amenable to reaction with, for example, an inorganic compound such that although the reaction takes place within the environment of a biological system, it is not susceptible to reaction with the endogeneous molecules of the biological system itself. Once the proto-drug and the activation drug react, the products of that reaction and their metabolites become compounds having well known biological behaviors that retain their properties in well explored and well studied fashion and under the addition of many chemical moieties. What will happen to these chemicals that go into making up the proto-drug is predictable over a wide range of chemical modifications. Mechlorethamine, as a specific example, remains a toxin to the biological tissues in which it is deposited for a large number of modifications—modifications well studied and understood. Thus, both the proto-drug precursor chemistries that are "a-biologic" and the chemistries of their corresponding pharmacologically active reaction products are sufficiently understood as to allow for determination of modifications that are the basis for any number of specific variations in the instant specification and that are amenable to expansion within known teaching.

The process for the detailed design of an assemblage includes the following process steps:

Selection of a Differentially Concentrating Moiety: A process step whereby chemical moieties of a compound having properties enhancing differential concentration, meaning that the ratio of the concentration of the said compound in the cancer or other targeted tissue or tissues as compared to the concentration of the compound in normal tissues will at some time during the pharmacokinetics of the drug as a result of absorption, distribution, metabolism, and elimination processes, become elevated, are identified by specific procedures. One method of selection of compounds containing a differentially selective moiety is HPLC. These HPLC procedures include, but are not limited to, subjecting candidate compounds containing (or consisting entirely of) the differentially concentrating moiety to a determination of diffusion rates through various types of HPLC columns to select for those having low diffusion rates (that is, high retardation rates). Examples of HPLC columns useful for this purpose are cancer cell RNA doped HPLC columns, cancer cell DNA doped HPLC columns and HPLC columns doped with cancer cells, cancer cell puree or cancer cell extract (otherwise referred to as "cancer-type columns"). The differentially concentrating moiety is also evaluated by a reference column, meaning an HPLC column doped with RNA or DNA from normal cells or doped with normal cells, normal cell puree or normal cell extract. A compound containing a differentially concentrating moiety is selected by comparing the diffusion rate of the compound on the HPLC cancer-type column to the diffusion rate on the reference column. Those compounds having low diffusion rates (i.e., high retardation rates on the cancer-type columns) are potential differentially selective moieties.

A second method of selection of compounds containing a differentially selective moiety involves chromatography techniques other than HPLC. These procedures include, but are not limited to subjecting candidate compounds containing (or consisting entirely of) the differentially concentrating moiety to a determination of diffusion rates through cancer cell RNA and or DNA doped chromatography columns, sheets, layers, surfaces or other configurations used in chromatography to select for those having low diffusion rates (that is, high retardation rates), relative to the diffusion rates determined through the reference chromatographic system. The candidate compounds containing (or consisting entirely of) the moiety may also be subjected to a determination of diffusion rates through cancer cell, cancer cell purée, or cancer cell extract doped chromatography columns, sheets, layers, surfaces or other configurations used in chromatography. As with the HPLC procedure, a differentially concentrating compound is selected by comparing the diffusion rate of the compound on the cancer doped system to the diffusion rate on the reference system.

A third method by which compounds containing a differentially selective moiety are chosen is by in vivo methodology. Introduction of the material into animal models having induced cancer growths and examination of biopsies taken at various time delays, or sacrifice of the animals at successive time delays so as to make possible a determination of the candidate material's concentration as a function of time in both the cancer tissues and in normal tissues are in vivo methods used to evaluate potential compounds with a differentially concentrating moiety.

A mechanism by which potential compounds containing differentially selective moieties can be chosen to be put through the above described screening methodologies involves selection of such compounds from lists of dyes having high staining properties used in cancer diagnostics. In this regard, it is to be noted that dyes are used to stain biopsy tissue samples taken from patients for the purpose of determining the presence of cancer, since the cancer cells have a high uptake of the particular dyes used for this purpose. Examples of such dyes are: hematoxylin and eosin stains used in sentinel lymph node mapping methods of evaluation in breast tissue biopsies of cancer patients, and cytokeratin used in immunohistochemical staining of biopsy tissue taken from the lymph nodes to diagnose micrometastatic disease (Pendas, et al., *Annals of Surgical Oncology* 7(1), 15–20, 2000, January–February). Other dyes having tissue selectivity that translates into tumor selectivity include Nile blue (Lewis, et al. *Cancer Res.* 9, 736, 1949). In addition, we have noted that the yellow thioxanthones display tissue selectivity (Miller, et al. U.S. Pat. No 5,346, 917). The selectivity of these dyes, coupled with their favorable physicochemical properties, makes them good candidates for the selective delivery of drugs.

A list of such dye materials that are compounds containing, or consisting entirely of potential differentially selective moieties includes, but is not limited to the following: Nile blue; thioxanthones; hematoxylin stain; eosin stain; cytokeratin stain; DNA/RNA stains including trypan-blue, methyl-green, ethidium bromide, leucofuchsin dye, methylene blue; materials in references as *Handbook of Fluorescent Probes and Research Chemicals* [by Richard P. Haugland, Sixth Edition] including the stains Acridine homodimer, acridine orange, actinomycin D, 7-aminoactinomycin D, 9-Amino-6-chloro-2-methoxy-acridine, 4,6-diamidino-2-phenylindole, dihydroethidium, 4',6-(diimidazolin-2-yl)-2-phenylindole, ethidium-acridine heterodimer, ethidium diazide, ethidium homodimer-1 and -2, ethidium monoazide, hydroxystilbemidine, methane-sulfonate; general purpose biological stains such as safranin, malachite green, eosin yellowish, crystal violet, methylene blue, hematoxylin, bismarck brown, carmine alum, methyl green, and neutral red, Giemsa stain, and Gram stain, and chemicals known to 'adhere to' but not bind to DNA and RNA sometimes referred to as impermanent stains.

The list of potential dyes and biological stains for the differentially selective moiety is long. Choosing preferred candidates for a chemical moiety having properties enhancing differential concentration must be confirmed by one or more of the previously described selection methods.

Of particular concern is that the selected material be of low toxicity to normal tissue and to the extent that it manifests any toxicity, that the toxicity be differentially selective against the cancer tissues (otherwise the said characteristic would compete against the overall drug design). This particular concern aided in the selection of the differential concentration moiety of the proto-drug of Formulas I and II, given below.

Selection of a Toxic Moiety: A process step whereby a chemical moiety having properties of causing or enhancing cytotoxicity or cell death is determined by in vitro tests, in vivo tests, or is selected from existing lists of compounds known to have cytotoxic properties and that contain a cytotoxic moiety.

Selection of a Cap Moiety: A process step whereby chemical moieties having the property of masking, capping, mollifying or eliminating the cytotoxicity of the toxic moiety together with the property that such a cap moiety is not chemically removed by enzymatic or other metabolic processes in the body of the patient, are determined by in vitro tests, or are selected from existing lists of reagents with the toxic moiety selected as described above. The adequacy of the cap moiety is ascertained subsequent to the formation of the complete proto-drug (including the selected linkages as discussed herein below). More specifically, the proto-drug is tested for adequacy in vitro or in animal models, or in human subjects. The metabolic eliminates, by-products, or extracts from the test system are evaluated by HPLC or other analytical methods to confirm that the proto-drug has not been metabolized or modified in such a way as to yield a toxin when applied or administered alone (i.e., in the absence of the activation drug).

Selection of an Activation Drug: A process step whereby one or more chemical compounds separate from the proto-drug having the property of removing the mask or cap moiety, or a sufficiency of the mask or cap, or so modifying the chemistry of the overall proto-drug molecule as to substantially eliminate the masking or capping function of the mask or cap thereby making the residual compound toxic, or so as to cause the proto-drug to release a toxic moiety within the body of the cancer patient and in the environs of the cancer cells.

Selection of the Linkages of the Proto-Drug: The selected chemical moiety or moieties having properties enhancing differential concentration, the selected chemical moiety or moieties having toxic properties, and the selected chemical moiety or moieties having the property of capping the cytotoxicity of the overall chemical compound (i.e., the proto-drug) must be linked by either chemical bonds or a combination of chemical bonds and atoms between the several moieties that will chemically hold the moieties together allowing therein each moiety to facilitate the individual functions for which each moiety was selected. These connections between the moieties are referred to as the linkages. Generally, the method of linkage of each pair of moieties will be chosen according to existing teaching regarding methods of bonding so as to avoid the modification of the individual properties of the moieties selected e.g., recognizing therein that the cap moiety serves to inhibit the activity of the toxic moiety until the addition of the activation drug. In general, for each compound selected to become (after bonding or linking) a moiety of the new proto-drug, one determines the sites responsible for the desired properties of the selected compound; it is important that these sites not be substantially disturbed or modified by the linkages. Modifying the molecule at the several available bonding positions allows one to test and determine the sites responsible for the desired properties. The individual molecules selected to provide differentially concentrating and toxic properties for the proto-drug are then attached at bonding positions situated away from the sites active for the particular trait for which the moiety has been selected; the individual molecule providing the cap moiety is then attached at a position so situated as to inhibit the activity of the toxic moiety. This procedure has been carried out in the process of the disclosure, resulting in the examples of the present invention.

As a result of the process of the disclosure used to design the assemblage, the present invention provides proto-drugs of Formula I and II

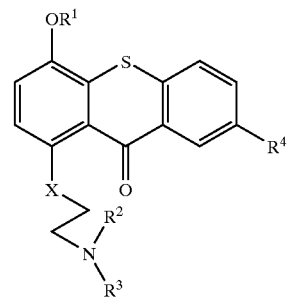

Formula I

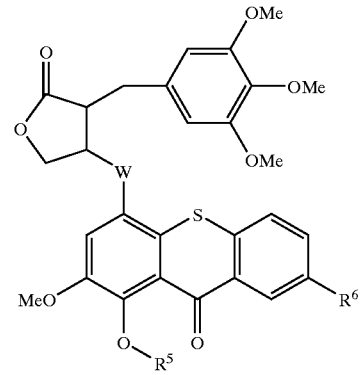

Formula II wherein:
$R^1$ is $SiZ_3$;
$R^2$ is methyl, chloroethyl, hydroxyethyl, or bromoethyl;
$R^3$ is chloroethyl, hydroxyethyl, or bromomethyl;
$R^4$ is H, $SO_3H$, or taurine;
$R^5$ is $SiZ_3$;
$R^6$ is H, $SO_3H$, or taurine;
each Z of $Z_3$ is independently t-butyl or methyl;
X is carbon, oxygen, or nitrogen; and
W is carbon, oxygen, or nitrogen.

The present invention further provides a method of selectively delivering a cytotoxic compound to tumor tissue by the use of a proto-drug having a moiety that differentially concentrates, a cytotoxic moiety and a cap moiety, whereby the proto-drug delivers the toxic moiety in such a manner as to prevent significant damage to normal tissues by maintaining the cap moiety on the proto-drug until the proto-drug differentially concentrates in the tumor tissue during a time delay period, and after such time delay the proto-drug produces a cytotoxic compound upon administration of an activation drug.

Another object of the present invention is to provide a method of selectively delivering a cytotoxic compound to tumor tissue by administering a proto-drug of Formula I or II

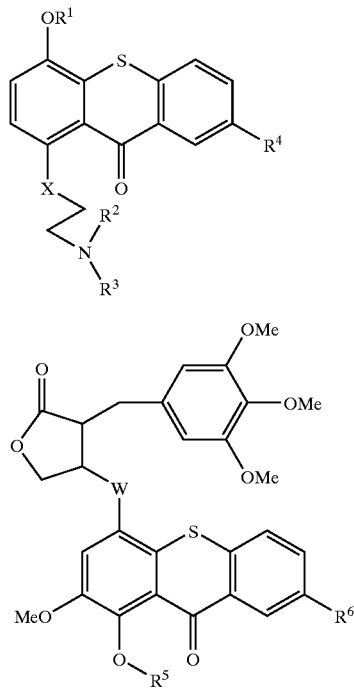

Formula I

Formula II whereby:

$R^1$ is $SiZ_3$;

$R^2$ is methyl, chloroethyl, hydroxyethyl, or bromoethyl;

$R^3$ is chloroethyl, hydroxyethyl, or bromomethyl;

$R^4$ is H, $SO_3H$, or taurine;

$R^5$ is $SiZ_3$;

$R^6$ is H, $SO_3H$, or taurine;

each Z of $Z_3$ is independently t-butyl or methyl;

X is carbon, oxygen, or nitrogen; and

W is carbon, oxygen, or nitrogen so that the proto-drugs of Formulas I and II deliver the toxic moiety in such a manner as to prevent significant damage to normal tissues by maintaining the proto-drug's cap moiety intact until the proto-drug differentially concentrates in the tumor tissue during a time delay, and after such time delay the proto drug produces a cytotoxic compound upon administration of a fluoride salt.

Yet another object of the disclosure provides compounds of Formulas III and IV

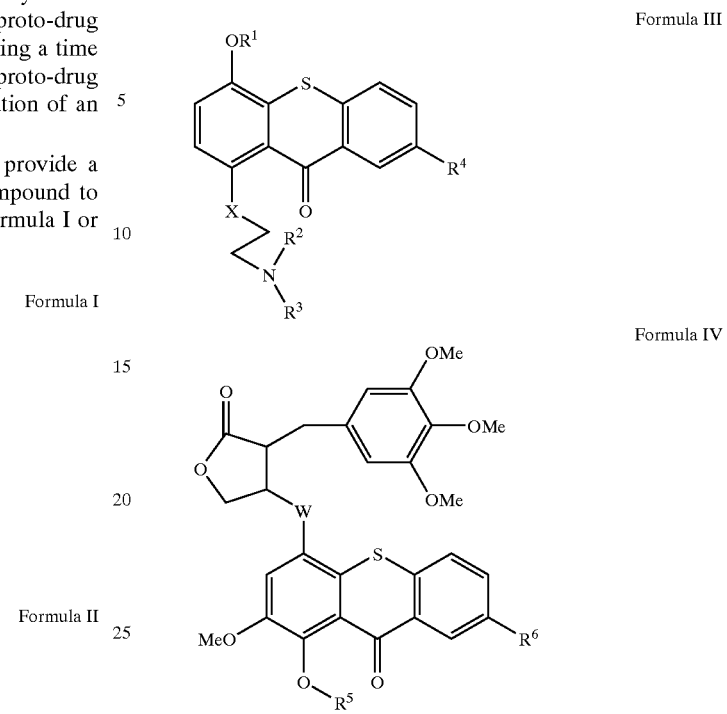

Formula III

Formula IV wherein:

$R^1$ is H;

$R^2$ is methyl, chloroethyl, hydroxyethyl, or bromoethyl;

$R^3$ is chloroethyl, hydroxyethyl, or bromomethyl;

$R^4$ is H, $SO_3H$, or taurine;

$R^5$ is H;

$R^6$ is H, $SO_3H$, or taurine;

X is carbon, oxygen, or nitrogen; and

W is carbon, oxygen, or nitrogen or a pharmaceutically acceptable base addition salt of Formulas III and IV.

This invention also provides a method of evaluating anticancer activity for compounds of Formulas I and II with (or in the case of Formulas III and IV, without) the activation compound, such method to be used in concert with the process for the detailed design for an assemblage and used in the process steps as detailed above, or for the in vitro and in vivo evaluation of the anticancer activity of any other chemical substance.

This invention also provides the use of a compound of Formula I or II with, or in the case of Formulas III and IV without the activation compound, for the manufacture of a medicament for the treatment of neoplasms. Additionally, this invention provides a pharmaceutical preparation for the treatment of neoplasms comprising an effective amount of a compound of the Formula I or II together with pharmaceutically acceptable excipients, and an activating amount of a fluoride salt together with pharmaceutically acceptable excipients, whereby the compound of Formula I or II and the activation drug are packaged for individual administration. Furthermore, this invention includes a method for the treatment of neoplasms comprising administering an effective amount of compounds of the Formula I or II, waiting for a time delay period and administering an activating amount of a fluoride salt.

The compounds of the invention, namely the proto-drug and the activation drug, can be administered orally, intraperitoneally (ip), intravenously (iv), percutaneously, intramuscularly, intranasally, or intrarectally. The route of administration will vary depending on the particular drug being administered, the disease being treated, the convenience of the patient and the caregiver, and other relevant circumstances.

The pharmaceutical compositions of the invention are prepared by procedures well known in the pharmaceutical art. The carrier or excipient may be solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like. Preferred compositions and preparations of the present invention may be determined by methods well known to the skilled artisan.

The compounds of the present invention may be administered orally, for example, with an inert diluent in a capsule or compressed tablet dosage form. For the purpose of oral therapeutic administration, the compounds may be incorporated with excipients and used in the form of tablets, pills, troches, capsules, elixirs, suspensions, syrups, wafers, chewing gums and the like. The active ingredient in these preparations can vary in concentration from as little as about 0.001% to about 70% of the weight of the unit. The amount of the compound present in compositions is such that a suitable dosage will be obtained. The dose range of the proto-drug and activation drug, based on customary practice of projecting from animal models for the treatment of humans is about 1 $\mu$g/kg to about 25 $\mu$g/kg.

On a one-to-one molarity basis, the activation drug dosage can be reduced by a factor of 10. The higher than one-to-one molarity basis for the activation drug is given to enhance the efficacy and speed of the activation process. In the case of children, elderly or the exceptionally infirm, dosages of the proto-drug and of the activation drug as much as ten times lower than would routinely be used may be required. Because experiments have shown that the unactivated proto-drug is of exceptionally low toxicity, more aggressive cancers may require dosages of the proto-drug and of the activation drug as much as ten times higher than for less aggressive disease.

The tablets, pills, capsules, troches, and the like may also contain one or more of the following adjuvants: binders such as povidone, hydroxypropyl cellulose, microcrystalline cellulose, or gelatin; excipients or diluents such as starch, lactose, or dicalcium phosphate; disintegrating agents such as sodium starch glycolate and the like; lubricants such as magnesium stearate, stearic acid, or talc; wetting agents such as sodium lauryl sulfate or polysorbates; sweetening and flavoring agents such as sucrose, aspartame, peppermint and other natural and synthetic flavors. When in capsule form the dosage may contain a liquid carrier such as fatty oil. Tablets may be coated with sugar and binders or materials such as polymethacrylates, or other coating agents.

Time Delay Toxin Activation and the Time Delay Period

Toxicity arises from chemical reactions that destroy compounds vital to normal cell functions or from the production of compounds that disrupt cell metabolic processes. The cumulative toxic damage produced in the cell at any time is proportional to the exposure of the cell to the toxins, that is, to the toxic exposure. Therefore, to achieve selective toxicity in the treatment of cancer, it is vital to consider the differences in the metabolic rates that exist between normal tissues and malignant neoplastic tissues, as, for example, has been done in the work of Chello et al., *Cancer Res.*, 37:4297, 1977. Furthermore, the difference between the metabolism of compounds by neoplastic and normal cells has led to the development of chemical tests for the presence of cancer (Anderson, et. al., *Cancer Res.*, 30, 1344 (1970); Dewanjee, et. al., *J. Nucl. Med.*, 14, 624 (1973); Henderson, et. al., *Cancer Res.*, 25, 1018 (1965); Holland and Sleamaker, *Acta Cytol.*, 13, 246 (1969); Málek et. al., *Cas. Lek. Cesk.*, 1, 16 (1963); Philips, et. al., *Am. J. Surg.*, 100, 384 (1960); and Rall et. al., *J. Natl. Cancer Inst.*, 19, 79 (1957)).

The timing of the administration of the proto-drug and the activation drug is critical if the proto-drug concentration differential between the cancer cells and the normal cells is to be advantageously used to produce a nontoxic, effective treatment. Chemically triggered time delay toxin activation ("TDTA"), originally proposed by E. H. Walker in 1980, envisioned two compounds to be administered separately—with a time delay between the administration of the prodrug, the first drug in the sequence, and the administration of the activation drug, the second in the sequence. In that proposal the prodrug was limited to two moieties, the toxic moiety and the mask or cap moiety. In the current invention the proto-drug requires at least three parts: the differentially concentrating moiety, the toxic moiety, and the mask or cap moiety. The differentially concentrating moiety is an essential delivery moiety of the proto-drug, providing the complete molecule with a cytometabolic rate differential that with time increases the concentration of the proto-drug in cancer cells and tissues as compared to the proto-drug concentration in normal cells and tissues of the body. The second drug administered, the activation drug, activates the initially administered proto-drug by removing or modifying the action of the cap moiety of the proto-drug. Individually each of these two drugs is designed to be substantially non-toxic (i.e., substantially biologically inert) when administered alone in dosage strengths. Combined, however, these two react to form or to release an anticancer cytotoxin (i.e., a pharmacologically active agent). The TDTA mechanism takes advantage of the neoplastic to normal tissue proto-drug concentration ratio rise with time that can occur as a result of the pharmacokinetics of agents having differing and favorable metabolic absorption and elimination rate coefficients, as discussed below. High uptake and low elimination rates in the neoplastic tissue relative to these rates in normal tissues favors the long-term rise in the concentration ratio. By measuring the kinetics of the process, as has been done to establish dosages and time delays in the application of the examples of the present disclosure, toxicity can be avoided in the normal tissues and efficacy in the treatment of the cancerous tissues can be effected. The mechanism involved in TDTA is fundamentally distinct from prior chemotherapeutic approaches to toxin specificity, including those approaches involving prodrugs, latent activation drugs, and chemically targeted or site-binding drugs. While binding of the differentially concentrating moiety to a cell site as an aid to delivery can be employed, the present proto-drug design is not so limited as to require such binding to create a concentration differential and is therefore more flexible as a method of drug delivery design.

In the pharmacokinetics of normal and neoplastic tissues, uptake and elimination of metabolic products are governed by the chemical kinetics of cells and the physical processes of diffusion, membrane permeability, active transport, blood circulation, and excretion. To a considerable extent, drug concentrations can be predicted from first-order kinetics equations (see below). The loss of a drug from serum (the drug reservoir) following intravenous injection, for example, follows chemical kinetics in which uptake by body tissues takes place on a molecule-by-molecule basis (i.e., in essence the drug molecules do not react with each other). This scenario is described by equation (1), which indicates that rate of loss from the reservoir is proportional to concentration:

$$dD/dt = -pD \qquad (1)$$

where D is the drug concentration (e.g., the proto-drug concentration) in the reservoir, t is the time, and p is a proportionality constant. Equation (2) demonstrates an exponential dependence of the drug concentration in the reservoir that is available to the tissues at any moment:

$$D = D_o e^{-pt} \qquad (2)$$

where $D_o$ is the initial serum drug concentration (at the moment of injection). The concentration C of the drug in the tissue will depend on the drug supply in the reservoir (leading to its increase by diffusion into the cells) and the rate at which such drug is removed from the tissue. This gives the rate equation:

$$dC/dt = gD - bC \qquad (3)$$

where g and b are rate coefficients. If the concentration of the drug in the tissue is initially zero, equation (3) has the solution represented by equation (4):

$$C = k(1 - e^{-at})e^{-bt} \qquad (4)$$

where $k = gD_o/a$ and $a = p - b$. The concentration-versus-time dependence given by equation (4) is encountered in tests of uptake and removal of nutrients and drugs in tissues. Data demonstrating a concentration-versus-time pattern for several compounds and differing murine tissues was reported in *Cancer Research*, 15:365, 1955 by H. Bush. The present inventors have also carried out similar experiments with compounds containing the thioxanthone moiety showing this same behavior in various murine tissues over time.

Consider the circumstance where a >> b, that is, when uptake is rapid. The exposure of a cell to the presence of the drug, represented by E, would then be given by the integral of C, specifically $$E = \int_o^\infty C \, dt = k \int_o^\infty e^{-bt} dt = k/b \qquad (5)$$

For two cell types having elimination constants $b_A$ and $b_B$, the exposure ratio would be $$R = E_A/E_B = b_B/b_A \qquad (6)$$

This means that the exposure to a slow acting toxin would only be in proportion to the ratio of the diffusion constants for the two cell types. Because, however, the chemistries of cancer and normal cells are similar, the expected exposure ratio will usually be modest—resulting in the failure to achieve differential toxicities in the treatment of cancers.

If the toxin of the proto-drug is masked for a time delay period T (also referred to as "time delay"), equation (5) becomes $$E = \int_T^\infty C \, dt = k \int_T^\infty e^{-bt} dt = k \, e^{-bT}/b \qquad (7)$$

where E is now a function of the time delay T. In such a case, the exposure ratio becomes $$R = E_A/E_B = (b_B/b_A) \exp[(b_B - b_A)T] \qquad (8)$$

Equation (8) shows that if the elimination rate for cell type B is larger than that for cell type A, the exposure ratio R can be made as large as desired if the time delay for activation is also made large enough.

Equation (8) represents the essence of the TDTA strategy, whereby the exposure ratio given by equation (8) can significantly exceed that ratio given by equation (6). The usefulness and validity of this novel approach to the design and development of cancer formulas, pharmaceuticals, and application protocols has been confirmed through the testing of proto-drugs, activation drugs, and assemblages in this disclosure.

In order to convert the substantially biologically inactive proto-drug to a pharmacologically active compound, however, an activation drug must be administered. As with the proto-drug, the concentration of the activation drug will be affected by the loss of the activation drug from the serum reservoir following its administration; this process can be represented by an equation of the same form as equation (1), which demonstrates that the rate of loss from the reservoir is proportional to concentration:

$$dA/dt = -qA \qquad (9)$$

where A is the activation drug concentration in the reservoir after the injection time t, where t > T, and q is the proportionality constant for the activation drug (corresponding to p in equation (1) for the proto-drug). Equation (10) yields an exponential dependence of the drug concentration in the reservoir available to the tissues at any moment:

$$A = A_o e^{-qt}, \quad t > T \qquad (10)$$

where $A_o$ is the initial serum concentration at the moment of injection, t=T, and A=0 for 0 < t < T.

Just as the proto-drug entered the individual cells and tissues of the body according to equation (3), so too will the activation drug enter the individual cells. However, as the drug enters the cells, reactions begin between the proto-drug and the activation drug, affecting the time development of both drugs in the body. Under such conditions the equations become:

$$dC/dt = \begin{cases} gD - bC, & 0 < t < T \\ gD - bC - rBC, & t > T \end{cases} \qquad (11)$$

and $$dB/dt = \begin{cases} 0, & 0 < t < T \\ fA - eB - rBC, & t > T \end{cases} \qquad (12)$$

where r is the reaction rate coefficient, f is the diffusion rate coefficient for the activation drug into the tissues and cells having concentration A. In other words, f for the activation drug corresponds to g for the proto-drug. Similarly, e is the coefficient for B and correspondingly b is the coefficient for C.

Next, the reaction between the proto-drug and the activation drug produces the toxin in the cells. The concentration of this toxin, J, is given by:

$$dJ/dt = \begin{cases} 0, & 0 < t < T \\ rBC - hJ - jJK, & t > T \end{cases} \qquad (13)$$

where h is the rate coefficient for the loss of the toxin from the cell, and jJK gives the reaction rate for the toxin with the vital cell chemistry at a rate given by j, K being the concentration of the compound or compounds of the cell chemistry, the loss of which causes cell death. The rate at which this vital cell chemical component is destroyed also depends on both the concentration J of the toxin and on its own concentration K; this rate is given by:

$$dK/dt = \begin{cases} K_0, & 0 < t < T \\ -jJK, & t > T \end{cases} \quad (14)$$

where $K_o$ is the concentration value of K at t<T.

Equations (2), (10), (11), (12), (13), and (14) can be readily solved by numerical methods and are significant in that they provide the detailed time course for the administration of the activation drug relative to the administration of the proto-drug; furthermore, these six equations are useful for refining values for R as determined by equation (8) since equation 8 provides the approximate value of R. The solution of equation (14) also provides a more precise determination of the effects of toxin exposure that is only approximately given by equations (5), (6), and (7). However, because of their complexities, the use of the equations (2), (10), (11), (12), (13), and (14) are somewhat inconvenient to the elucidation of the advantageous means to enhancing the desired differential toxicity. For example, there is an optimum time delay period, T. Equation (8) demonstrates that whereas R will rise with the time delay T, the exposures $E_A$ and $E_B$ and the corresponding concentrations $C_A$ and $C_B$ will drop with T. As a result, time delays must be chosen that provide sufficient differential toxicity while still delivering the needed toxic dose to the targeted tissues. The optimum time T can then be fine-tuned to provide an accurate determination using the numerical methods for evaluating equations (2), (10), (11), (12), (13), and (14) already indicated.

Whereas the optimum time delay can be achieved by means of the calculations described above, it may be necessary to confirm the adequacy of dosages and of time delays by actual measurements. In laboratory animals this can be done directly, as the present inventors have done. These actual measurements for determining the time delay can be carried out on the complete proto-drug or on just the compound containing the differentially concentrating moiety, since it is this moiety that is critical in establishing the concentration differential between normal and cancerous tissue.

The data determining the optimum time delay of either the compound containing the differentially concentrating moiety or the proto-drug itself in animal models in vivo can be used to approximate the time delay in humans by the application of Kleiber's law to the animal data. Kleiber's law states: "The total metabolic rate for an organism scales as the body mass raised to the ¾ power." To determine time delay, however, the specific metabolic rate, meaning the rate per unit mass is required. The specific metabolic rate is obtained by dividing the above ¾ power Kleiber scaling factor by the ratio of the individual animal masses for the two species. This results in an overall -¼ power scaling factor for the specific metabolic rate. For example, in the case of extrapolating mouse model time delay data to humans, a comparison of the mouse body mass (e.g., 20 grams) to the human body mass (e.g., 80 kilograms) provides a ratio of 4,000. Applying Kleiber's law, as adapted for calculating the specific metabolic rate to this ratio, it is estimated that the human specific metabolic rate is 8.0 times slower than the mouse. Hence, a 4 day time delay in a mouse translates to an approximate time delay of 32 days in a human. In the case of aggressive cancers where a higher risk is required to effect a greater chance of cure rate (i.e., where a greater than usually accepted toxicity to normal tissue would be tolerated so as to achieve an effective toxic level in cancer tissue), time delays shorter than those predicted by application of Kleiber's law to the animal model may be required. Also, for children, the elderly, and patients in very poor health, time delays longer than estimated by Kleiber's law may be necessary to ensure minimal toxicity to normal tissue. Time delays from a day to a couple of months are possible.

Where the time delay period is being used in human or veterinary clinics, eliminated metabolites of the proto-drug are monitored to determine when the toxic levels of proto-drug in normal tissues have dropped to safe levels (i.e., to determine when the activation drug should be administered). That is to say, one can establish beforehand the maximum dose of the toxin that can be safely tolerated by a patient. Monitoring the excretion of the metabolites using chemical assay procedures such as HPLC allows determination of the time when the proto-drug has reached safe levels in the normal tissues of the body—levels such that activation of the proto-drug will result in sufficiently low levels of the toxin in the normal tissues of the body. Administration of the activation drug at this time results in the maximum dose of toxin for the targeted cancerous tissues. If the level of the toxin in the targeted tissues is insufficient, then one must administer a higher initial dose of the proto-drug and use a longer time delay. If such modifications do not provide a sufficiently toxic dose in the targeted tissues on activation, then the differentially concentrating moiety, the toxic moiety, or both must be redesigned to provide superior pharmacokinetic parameters. The examples of the proto-drug and activation drug combinations as tested, however, have proved to have the necessary superior pharmacokinetic parameters.

The synergistic effects of pharmaceuticals are a known and frequently encountered hazard resulting from the administration of two or more drugs at the same time or in close time proximity to one another. By contrast, the present invention requires drug interaction and intends that when administered alone there will be little or no effect of each of the drugs individually on the body. Moreover, it is intended that the optimum time delays between administration of the proto-drug and the activation drug can be determined and used to avoid harmful side-effects of anticancer, disease fighting drugs.

The present invention further provides a method of selectively delivering a proto-drug and activating such proto-drug to become or release a cytotoxic compound in tumor tissue by waiting for a time delay and then administering an activation drug. The present invention further provides a method of selectively delivering the compounds of Formula I and Formula II and activating the compounds of Formulas I and II to become or release a cytotoxic compound in tumor tissue by waiting for a time delay and then administering sodium fluoride.

The present invention also provides a method of treating neoplasms in a mammal comprising administering to a mammal in need of such treatment a therapeutically effective amount of a proto-drug comprising a differentially concentrating moiety, a toxic moiety, and a cap moiety, waiting for a time delay and then administering an activation drug.

The present invention yet also provides a method of treating neoplasms in a mammal comprising administering to a mammal in need of such treatment a therapeutically effective amount of a compound of Formula I or II

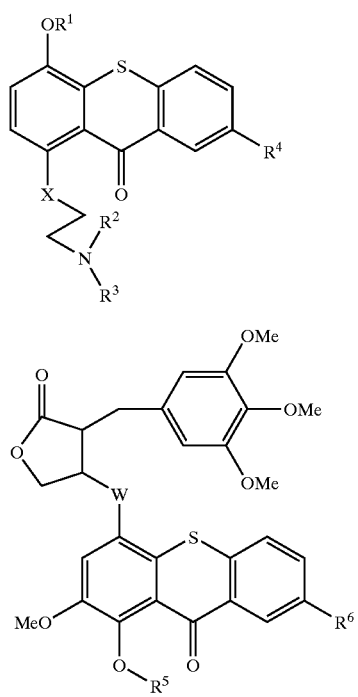

Formula I

Formula II wherein:
R¹ is SiZ₃;
R² is methyl, chloroethyl, hydroxyethyl, or bromoethyl;
R³ is chloroethyl, hydroxyethyl, or bromomethyl;
R⁴ is H, SO₃H, or taurine;
R⁵ is SiZ₃;
R⁶ is H, SO₃H, or taurine;
each Z of Z₃ is independently t-butyl or methyl;
X is carbon, oxygen or nitrogen; and
W is carbon, oxygen, or nitrogen
waiting for a time delay and then administering sodium fluoride.

Methods for In Vitro Testing

In vitro methods used to evaluate compounds and assemblages of the present invention rely on principles common to many systems presently available. For example, monolayer or suspension cells are plated, treated with the proto-drug, and incubated under appropriate conditions for the particular cell type.

Several parameters of cell health are then calculated or estimated throughout the test period (e.g., 7 days). If the assemblage (i.e., the proto-drug and the activation drug) is to be evaluated by an in vitro method following a time delay period, (e.g., 3 days of incubation) the activation drug is added to the appropriate wells and the testing continues for an additional period (e.g., 4 days).

The concentration of drug that causes cell kill or growth arrest in 50% of the population, $IC_{50}$, is calculated by a comparison between the drug-treated wells and untreated controls. Another useful parameter that can be determined by in vitro methods is the activity of the drug versus time. This parameter is of particular importance for those drugs that are slow acting due to metabolic reactions or poor absorption.

Murine Tumor Assays

Inhibition of tumors transplanted into mice is an accepted procedure for studying the efficacy of anti-tumor agents. Customarily the procedure is performed by trocar subcutaneous implantation of pieces of a tumor extracted from a carrier mouse, or by subcutaneous injection of cancerous cells on the order of 5 million per animal.

EXAMPLES

The present disclosure presents details of the use of the present inventive process to design and evaluate an assemblage. Moreover, the invention includes specific molecule design (e.g. proto-drugs), means for the preparation of these compounds, details of their testing, and procedures for the determination of the time delay. The following examples are merely illustrative of the present invention and should not be considered as limiting the scope of the invention in any way.

Example I

The preparation of an assemblage as described by the novel process set forth above began with the selection of a differentially concentrating moiety. In order to narrow the search for suitable candidates, the process began with a review of the existing literature.

Information regarding benzophenoxazines suggested that the use of such compounds tied to a toxin would be effective if the toxic moiety could be activated after the drug had reached a differential concentration in the cancer tissue. However, benzophenoxazines otherwise have poor physicochemical properties (e.g., poor solubility), a problem that makes them not too attractive as delivery moieties. In addition to the benzophenoxazine dyes, other substances show tissue selectivity. Among those, the yellow thioxanthones display tissue selectivity and some anticancer activity (Miller, et al. U.S. Pat. No 5,346,917). The selectivity of these dyes, coupled with their favorable physicochemical properties, makes them good candidates for the selective delivery of drugs.

In Formula I, a yellow dye which is, a thioxanthone, has been selected for the differential concentration moiety of the proto-drug. Confirmation that a thioxanthone displays differentially concentrating properties was demonstrated by in vivo examination of normal and tumor tissues. The data from this study confirms that yellow thioxanthone has differentially concentrating properties.

Several mice with implanted palpable tumors (pancreas) were injected iv with 40 mg/kg of the thioxanthone yellow dye. Animals were sacrificed at 4 h, 1 day, 2 days, 3 days, 4 days, and 5 days following administration of the thioxanthone. The tumor, pancreas, stomach, part of the intestine, and liver were cut and minced in alcohol to extract the dye. The amount of dye from each tissue was evaluated quantitatively using HPLC. A higher concentration of the dye in tumor compared to other tissues initially was seen at 1 day post-administration. There was no significant amount of dye remaining in the normal tissue by days 3–4.

The data from this in vivo study were also used to determine the time delay for the proto-drug that contains this differentially concentrating moiety. An optimum time delay of 4 days in the mouse predicts a time delay of about 32 days in the human. In the mouse model, however, possible time delays ranged from 2.5 to 6 days, translating to a time delay range of 20 to 48 days in humans. In the case of aggressive cancers, shorter time delays, possibly as short as one day, may be necessary to provide the required level of toxicity in the tumor tissue. By contrast, a time delay of a couple of months may be necessary in the severely compromised patient.

The selection of a toxic moiety to be linked to the differentially concentrating moiety was carried out by a review of the existing literature. The powerful anticancer activity of mechlorethamine has long been attributed to the nitrogen mustard moiety of the molecule. It acts by alkylating biologically important cell constituents whose function is then impaired. The major indications for its clinical use include bronchogenic carcinoma, Hodgkin's disease, non-Hodgkin's lymphomas, lymphosarcoma, and chronic myelocytic or chronic lymphocytic leukemia. However, nitrogen mustard displays a wider spectrum of action in vitro than its clinical applications suggest. The limitation on its use in vivo is directly related to its toxicity (nausea, vomiting, anorexia, leukopenia thrombocytopenia, local irritation). Attempts have been made to improve its selectivity or delivery through its incorporation into a variety of compounds (for example, Haines, et al., *J. Med. Chem.* 30, 542 (1987); Alexander, et al., *Tet. Lett.* 27, 3269 (1991). Thus, mechlorethamine is an excellent candidate for delivery and the thioxanthone nucleus provides the appropriate vehicle to deliver it to the target tissues and cells. In the example of Formula I, a nitrogen mustard, specifically mechlorethamine, has been selected for the cytotoxic moiety of the proto-drug.

Another group of powerful anticancer agents is the natural podophyllotoxins, which have been used to treat brain tumors and acute granulocytic leukemias, among others. These substances act by inhibiting mitosis in a reproducing cell. Limitations in their use are similar to those of nitrogen mustard described above with anemia as an added toxicity. Again, these types of substances are good candidates for selective delivery using thioxanthones. In Formula II, a podophyllotoxin derivative has been selected for the cytotoxic moiety of the proto-drug.

Following the selection of the differentially concentrating moiety and the toxic moiety, a mask or cap moiety is required to complete the elements of the proto-drug. In Formulas I and II, an inorganic moiety, specifically a silicate, $SiZ_3$, (where each Z of $Z_3$ is independently t-butyl or methyl) has been selected for the masking or capping moiety of the proto-drug. This inorganic silicate moiety, $SiZ_3$, further has the chemical characteristic that it is highly reactive with fluoride salts, some of which are not significantly toxic. As a consequence, the moiety is removable by non-toxic or low toxicity chemical reactions that can occur within the patient's body.

A reaction of this type occurs when fluoride present in toothpastes reacts with the calcium present in teeth. The product formed, a fluoride of calcium, is a very stable and stronger material than the natural calcium salt present in teeth. This is an example of a displacement reaction driven by the formation of a more stable material. In the case of compounds of Formulas I and II, silicon ions have a strong attraction for fluoride, stronger than the attraction of sodium or potassium for fluoride; thus, a displacement reaction can occur when sodium or potassium fluoride encounters a silicon compound. The reaction is very selective and specific.

The resulting proto-drug must be activated by an activation drug. In the examples of Formulas I and II, an inorganic chemical, a fluoride salt, has been selected for the uncapping chemical that will react with the proto-drug. The specific fluoride salt, sodium fluoride, was chosen based upon its known chemical properties. This inorganic fluoride salt activation drug is particularly suited for reaction with the proto-drugs of Formulas I and II because it is highly reactive with the specific silicates used as the capping moieties in these compounds. Furthermore, sodium fluoride is not significantly toxic in the quantity needed to uncap such proto-drugs. As a consequence, the mask or cap moiety of the proto-drug is removable by a very non-toxic inorganic chemical that occurs by a reaction within the patient's body without adverse effects on the patient.

Example II

Given below are the details of the synthesis of the proto-drug of Formula I.

Preparation Scheme I

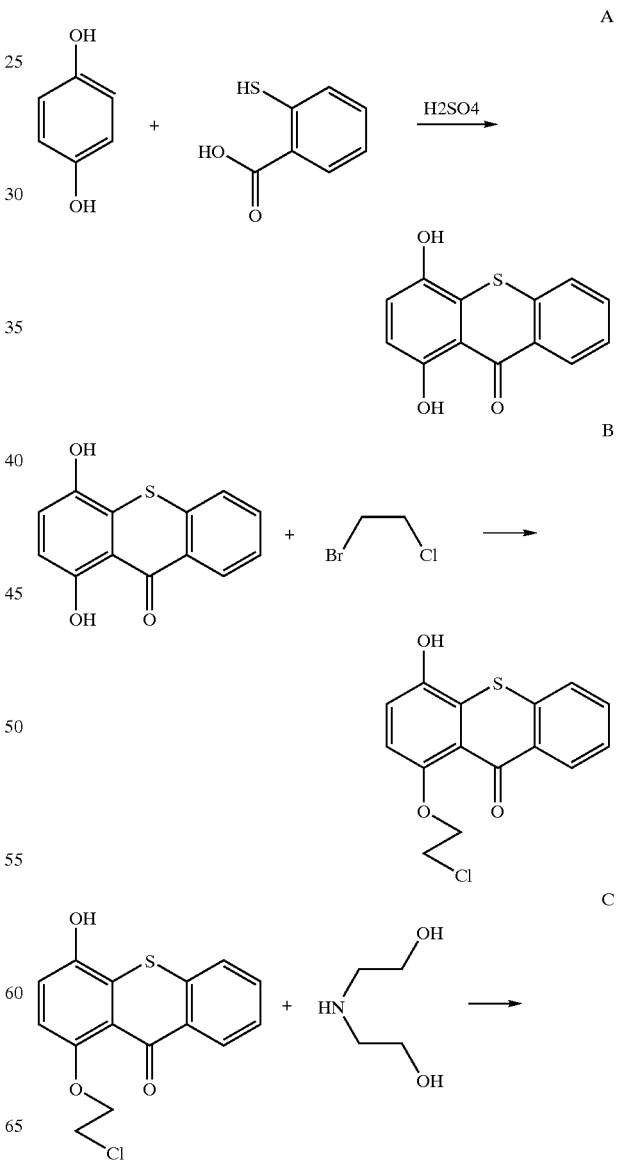

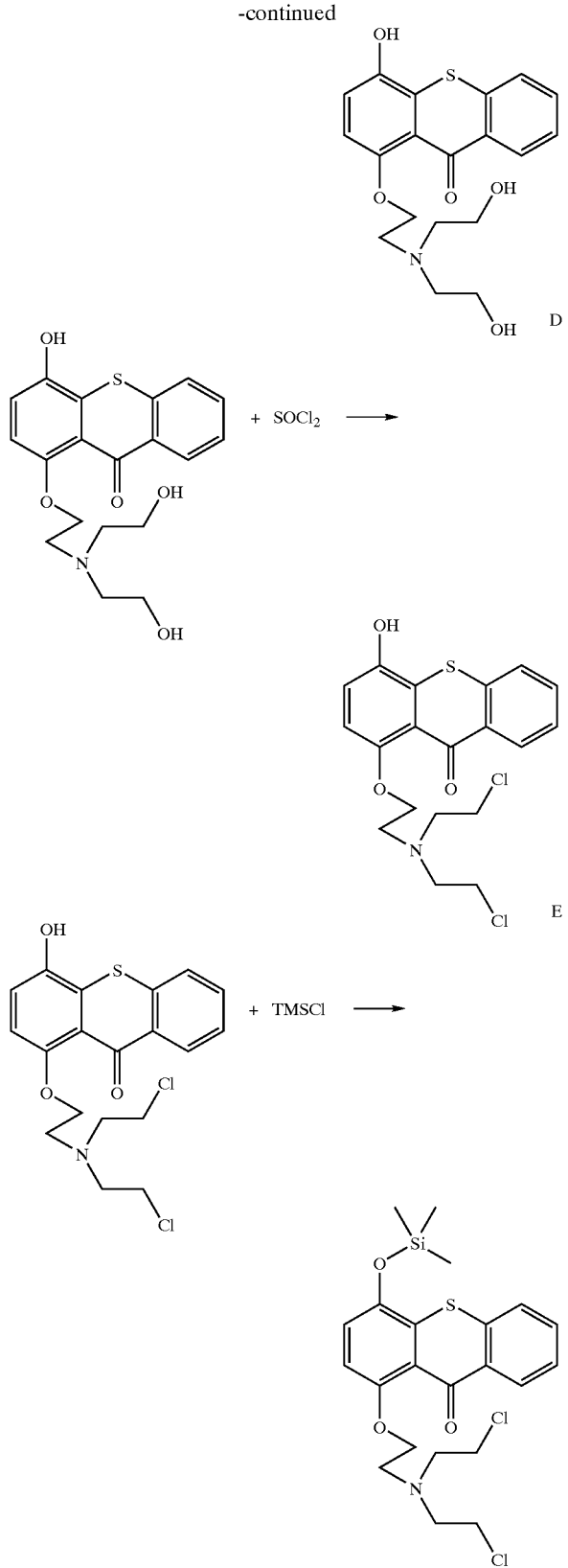

stirred at room temperature for 4 h. The red suspension is poured on ice and allowed to reach ambient temperature when it is then filtered. The solid obtained is treated with saturated sodium bicarbonate and the solution was carefully neutralized with 20% hydrochloric acid. The solid is filtered, dissolved in acetone and filtered again through a plug of silica gel. The solution is concentrated and the solid purified by column chromatography with silica gel using a mixture of hexanes: ethyl acetate (1:1) as the eluent. The fraction containing the product is concentrated under reduced pressure to provide the yellow title compound (2.36 g, 30%).

FDMS; m/e=244 (M$^+$)

Preparation 2

1-Chloroethoxy-4-hydroxythioxanthone

A solution of 120 mg of 1,4-dihydroxythioxanthone in 100 ml of acetone is stirred for 0.5 h at room temperature with 138 mg of potassium carbonate. A solution of 80 mg of 1-bromo-2-chloroethane in 5 ml of acetone is then added and the mixture refluxed for 24 h. The heterogeneous mixture is cooled, filtered, concentrated under reduced pressure and purified by silica gel column chromatography using a 1:1 mixture of hexanes and ethyl acetate to produce 100 mg of a yellow-red crystals (65%).

FDMS; m/e=307 (M$^+$)

Preparation 3

1-(N,N-bisdiethanolaminoethoxy)-4-hydroxythioxanthone

A solution of 0.5 g of 1-chloroethoxy-4-hydroxythioxanthone in 5 ml of diethanolamine is heated under nitrogen at 110° C. for 1 h. After cooling, water is added and the mixture extracted four times with ethyl acetate. The ethyl acetate extract is washed with water, dried with sodium sulfate, concentrated and purified by alumina column chromatography using ethyl acetate: ethanol (4:1) as the eluent solvent. The material obtained is crystallized from acetone to give 0.23 g (38%) of the yellow product.

FDMS; m/e=376 (M$^+$)

Preparation 4

1-(N,N-bischloroethylaminoethoxy)-4-hydroxythioxanthone

Method I: A solution of 0.5 g of 1-(N,N-bisdiethanolaminoethoxy)-4-hydroxythioxanthone in 5 ml of thionyl chloride is heated to reflux for 6 h. The excess thionyl chloride is removed by distillation, and the remaining solid is put through an alumina column chromatography using ethyl acetate: hexanes (1:1) as the eluent produced 0.3 g (58%) of a yellow solid.

FDMS; m/e=413 (M$^+$)

Method II: A solution of 0.5 g of 1-(N,N-bisdiethanolaminoethoxy)-4-hydroxythioxanthone in 10 ml of pyridine is treated at low temperature and under nitrogen with 0.4 g of methanosulphonyl chloride and the mixture kept under refrigeration for 24 h. The mixture is then poured in water and extracted with ethyl acetate. The ethyl acetate extract is washed with water, dried over sodium sulfate and concentrated to a yellow solid. This solid is dissolved in dimethylformamide (5 ml) and stirred under nitrogen at 80° C. with 3 g of lithium chloride for 24 h. The mixture is cooled, mixed with water and extracted with ethyl acetate. The ethyl acetate extract is washed with water, dried with sodium sulfate and concentrated. Purification via alumina chromatography using ethyl acetate:hexanes (1:1) as the eluent produces 0.37 g (71%) of the yellow solid.

FDMS; m/e=413(M$^+$)

Preparation 5

1-(N,N-bischloroethylaminoethoxy)-4-tert-butyldimethylsilyloxythioxanthone

Preparation 1

1,4-Dihydroxythioxanthone

A suspension of thiosalicylic acid (5.0 g) and hydroquinone (5.0 g) in concentrated sulfuric acid (100 ml) is A solution of 0.50 g of 1-(N,N-bischloroethylaminoethoxy)-4-hydroxythioxanthone in 10 ml of dimethylformamide is mixed with 0.22 g of tert-butyldimethylsilyl chloride, 0.20 g of imidazole and a catalytic amount of dimethylaminopyridine, and stirred at room temperature for 12 h. The solution is then added over water and extracted with ethyl acetate. The ethyl acetate extract is washed sequentially with saturated sodium bicarbonate and water, dried over sodium sulfate, concentrated and dissolved in a mixture of ethyl acetate: hexanes (1:4) and passed through a plug of alumina. The solid obtained after concentration is pure and weighed 0.48 g (70%).

FDMS; m/e=527 (M$^+$)

Example III 1-(N-chloroethyl-N-methylaminoethoxy)-4-hydroxythioxanthone

A solution of 0.5 g of 1,4-dihydroxythioxanthone in 20 ml of dimethylformamide is stirred for 0.5 h at room temperature with 6 g of potassium carbonate under anhydrous conditions. Mechlorethamine hydrochloride (0.4 g) is then added and the heterogeneous mixture was stirred for 12 h at 50° C. Water is added and the mixture extracted with ethyl acetate. The ethyl acetate solution is washed with water, dried with sodium sulfate, passed through a plug of alumina and concentrated under vacuum to produce 0.4 g (55%).

FDMS; m/e=364 (M$^+$)

Example IV

Compounds of Formula I were tested in vitro using murine lines of leukemia L1210 cells, pancreas tumor (Pan 03), Lewis lung carcinoma, and a normal fibroblast. The IC$_{50}$ value for all the assemblages, meaning a proto-drug of Formula I followed by the activation drug sodium fluoride, were lower than 0.4 micromolar for the cancerous tissues. Comparable values were obtained for the normal fibroblast cells in vitro. In the case of testing of the complete proto-drug without subsequent treatment with an activation drug, the IC$_{50}$ was 0.1 molar in normal cells. The test demonstrated that activation significantly altered the toxicity of the proto-drug.

Example V

A study of the activity of compounds of Formula I has been performed on mice using three tumor models: leukemia, lung and pancreas. A total of 5 animals per tumor line were used and treatment was initiated two weeks after implantation (late stage testing). The proto-drug compound was administered three times at a dose of about 30% that of the mouse LD$_{50}$ of the mechlorethamine toxic moiety, followed by the activation drug, sodium fluoride, dosed (in excess) at 5 times the molar equivalent, 4 days later.

Experiment: C57 male mice (5/tumor line) were implanted subcutaneously with ca. 1 million cancerous cells suspended in saline solution, and tumors were allowed to grow for 2 weeks when they were palpable. Test compound, 0.2 ml, was then administered ip as a suspension containing water, polyethylene glycol (3%) and alcohol (5%). The activator was administered 4 days later as an ip solution. Two more treatments were given with a week intermission between them.

Results: Lung tumors were unaffected by the treatment and animals were sacrificed before the end of the 30-day study. Treatment of leukemia infected animals produced 4 cures (out of 5 animals) as evidenced by disappearance of tumor; three of five animals implanted with pancreas tumor cells were cured following the drug treatment regimen. Cured animals were maintained beyond the 30-day study term. Other animals were sacrificed.

A second set of experiments produced 5/5 cures in both solid leukemia L1210 and pancreatic tumors.

We claim:

1. A compound of the Formula I:

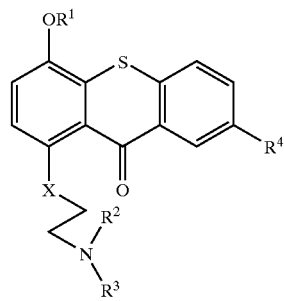

Formula I wherein:

$R^1$ is SiZ$_3$;

$R^2$ is methyl, chloroethyl, hydroxyethyl, or bromoethyl;

$R^3$ is chloroethyl, hydroxyethyl, or bromomethyl;

$R^4$ is H, SO$_3$H, or taurine;

each Z of Z$_3$ is independently methyl or t-butyl; and

X is carbon, oxygen, or nitrogen.

2. A compound of the Formula II:

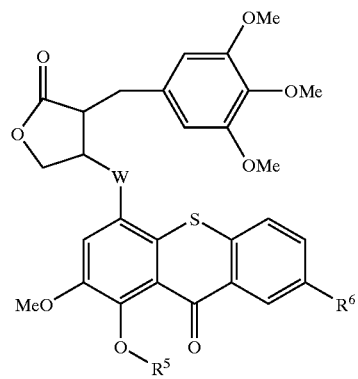

Formula II wherein:

$R^5$ is SiZ$_3$;

$R^6$ is H, SO$_3$H, or taurine;

each Z of Z$_3$ is independently methyl or t-butyl; and

W is carbon, oxygen, or nitrogen.

3. A compound of the Formula III:

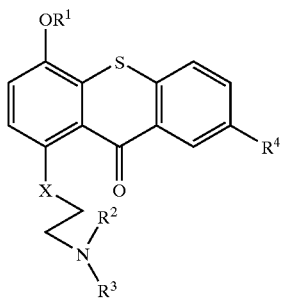

Formula III wherein:
R¹ is H;
R² is methyl, chloroethyl, hydroxyethyl, or bromoethyl;
R³ is chloroethyl, hydroxyethyl, or bromomethyl;
R⁴ is H, SO₃H, or taurine; and
X is carbon, oxygen, or nitrogen.

4. A compound of the Formula IV

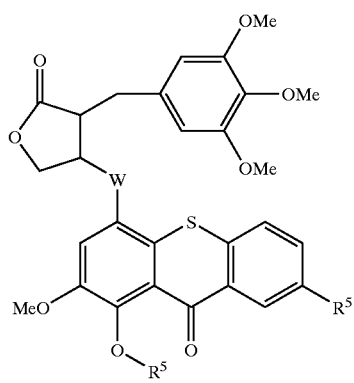

Formula IV wherein:
R⁵ is H;
R⁶ is H, SO₃H, or taurine; and
W is carbon, oxygen, or nitrogen.

5. A method of treating neoplasms in a mammal comprising:
(a) administering to a mammal in need of such treatment an effective amount of a compound of the Formula I:

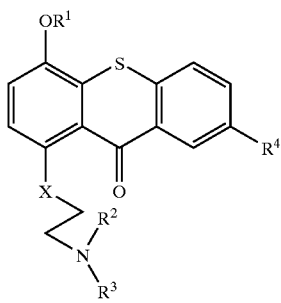

Formula I wherein:
R¹ is SiZ₃;
R² is methyl, chloroethyl, hydroxyethyl, or bromoethyl;
R³ is chloroethyl, hydroxyethyl, or bromomethyl;
R⁴ is H, SO₃H, or taurine;
each Z of Z₃ is independently methyl or t-butyl; and
X is carbon, oxygen, or nitrogen;
(b) waiting for a time delay period; and
(c) administering to the mammal an activating amount of a fluoride salt.

6. The method of claim 5 whereby the time delay period is from about 1 to about 32 days.

7. The method of claim 5 whereby the fluoride salt is sodium fluoride.

8. A method of treating neoplasms in a mammal comprising:
(a) administering to a mammal in need of such treatment an effective amount of a compound of the Formula II

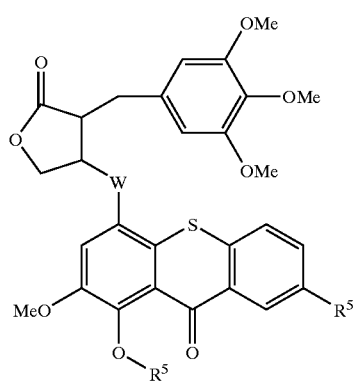

Formula II wherein:
R⁵ is SiZ₃;
R⁶ is H, SO₃H, or taurine;
each Z of Z₃ is independently methyl or t-butyl; and
W is carbon, oxygen, or nitrogen;
(b) waiting for a time delay period; and
(c) administering to the mammal an activating amount of a fluoride salt.

9. The method of claim 8 whereby the time delay period is from about 1 to about 32 days.

10. The method of claim 8 whereby the fluoride salt is sodium fluoride.

11. A method of treating neoplasms in a mammal comprising administering to a mammal in need of such treatment a therapeutically effective amount of a compound of the Formula III

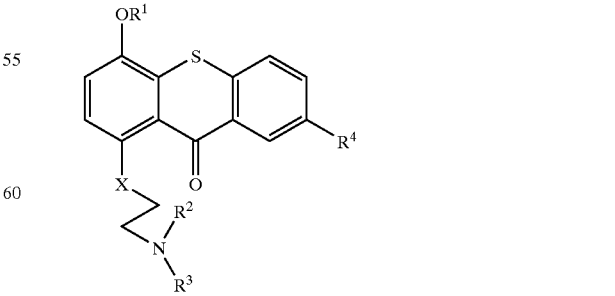

Formula III wherein:
R¹ is H $R^2$ is methyl, chloroethyl, hydroxyethyl, or bromoethyl;
$R^3$ is chloroethyl, hydroxyethyl, or bromomethyl;
$R^4$ is H, $SO_3H$, or taurine; and
X is carbon, oxygen, or nitrogen.

12. A method of treating neoplasms in a mammal comprising administering to a mammal in need of such treatment a therapeutically effective amount of a compound of the Formula IV

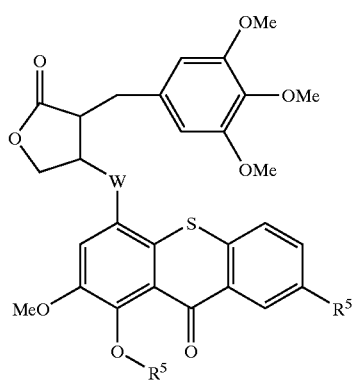

Formula IV wherein:
$R^5$ is H;
$R^6$ is H, $SO_3H$, or taurine; and
W is carbon, oxygen, or nitrogen.

13. A pharmaceutical preparation comprising:
(a) an effective amount of a compound of the Formula I

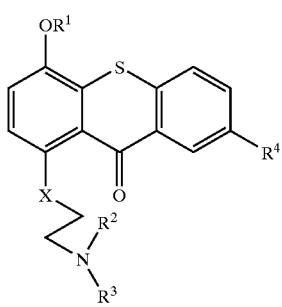

Formula I wherein:
$R^1$ is $SiZ_3$;
$R^2$ is methyl, chloroethyl, hydroxyethyl, or bromoethyl;
$R^3$ is chloroethyl, hydroxyethyl, or bromomethyl;
$R^4$ is H, $SO_3H$, or taurine;
each Z of $Z_3$ is independently methyl or t-butyl; and
X is carbon, oxygen, or nitrogen
together with a pharmaceutically acceptable excipient;
(b) an activating amount of a fluoride salt together with a pharmaceutically acceptable excipient;
whereby the compound of the Formula I and the fluoride salt are packaged for individual administration.

14. The pharmaceutical preparation of claim 13 whereby the fluoride salt is sodium fluoride.

15. The pharmaceutical preparation of claim 13 whereby the compound of Formula I is 1-(N,N-bischloroethylaminoethoxy)-4-tert-butyldimethylsilyloxythioxanthone.

16. A pharmaceutical preparation comprising:
(a) an effective amount of a compound of the Formula II

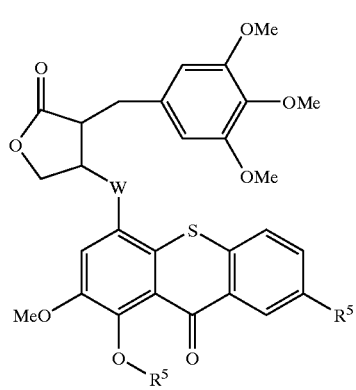

Formula II wherein:
$R^1$ is $SiZ_3$;
$R^6$ is H, $SO_3H$, or taurine;
each Z of $Z_3$ is independently methyl or t-butyl; and
W is carbon, oxygen, or nitrogen
together with a pharmaceutically acceptable excipient;
(b) an activating amount of a fluoride salt together with a pharmaceutically acceptable excipient;
whereby the compound of the Formula II and the fluoride salt are packaged for individual administration.

17. The pharmaceutical preparation of claim 16 whereby the fluoride salt is sodium fluoride.

18. A method for the preparation of 1-(N,N-bischloroethylaminoethoxy)-4-tert-butyldimethylsilyloxythioxanthone, such method comprising:
(a) combining thiosalicylic acid and hydroquinone in the presence of sulfuric acid to produce 1,4-dihydroxythioxanthone;
(b) combining the 1,4-dihydroxythioxanthone, potassium carbonate and 1-bromo-2-chloroethane in acetone under reflux to produce 1-chloroethoxy-4-hydroxythioxanthone;
(c) heating the 1-chloroethoxy-4-hydroxythioxanthone under nitrogen in the presence of diethanolamine, adding water and extracting with ethyl acetate to produce 1-(N,N-bisdiethanolaminoethoxy)-4-hydroxythioxanthone;
(d) heating the 1-(N,N-bisdiethanolaminoethoxy)-4-hydroxythioxanthone with thionyl chloride to reflux and then distilling off excess thionyl chloride to produce 1-(N,N-bischloroethylaminoethoxy)-4-hydroxythioxanthone; and
(e) stirring the 1-(N,N-bischloroethylaminoethoxy)-4-hydroxythioxanthone in dimethylformamide with tert-butyldimethylsilyl chloride, imidazole and a catalytic amount of dimethylaminopyridine at room temperature and then carrying out a water-ethyl acetate extraction to produce 1-(N,N-bischloroethylaminoethoxy)-4-tert-butyldimethylsilyloxythioxanthone.

19. A method for the preparation of 1-(N,N-bischloroethylaminoethoxy)-4-tert-butyldimethylsilyloxythioxanthone, such method comprising:
(a) combining thiosalicylic acid and hydroquinone in the presence of sulfuric acid to produce 1,4-dihydroxythioxanthone;

(b) combining the 1,4-dihydroxythioxanthone, potassium carbonate and 1-bromo-2-chloroethane in acetone under reflux to produce 1-chloroethoxy-4-hydroxythioxanthone;

(c) heating the 1-chloroethoxy-4-hydroxythioxanthone under nitrogen in the presence of diethanolamine, adding water and extracting with ethyl acetate to produce 1-(N,N-bisdiethanolaminoethoxy)-4-hydroxythioxanthone;

(d) combining the 1-(N,N-bisdiethanolaminoethoxy)-4-hydroxythioxanthone in pyridine with methanesylfonyl chloride under nitrogen to produce a mixture that is maintained under refrigeration, extracting the mixture with water-ethyl acetate to produce a solid, after which such solid is dissolved in dimethylformamide, heated and stirred under nitrogen with lithium chloride, adding water and extracting with ethyl acetate to produce 1-(N,N-bischloroethylaminoethoxy)-4-hydroxythioxanthone; and (e) stirring the 1-(N,N-bischloroethylaminoethoxy)-4-hydroxythioxanthone in dimethylformamide with tert-butyldimethylsilyl chloride, imidazole and a catalytic amount of dimethylaminopyridine at room temperature and then carrying out a water-ethyl acetate extraction to produce 1-(N,N-bischloroethylaminoethoxy)-4-tert-butyldimethylsilyloxythioxanthone.

20. A process for the preparation of 1-(N-chloroethyl-N-methylaminoethoxy)-4-hydroxythioxanthone, such process comprising:

(a) combining 1,4-dihydroxythioxanthone in dimethylformamide with potassium carbonate at room temperature under anhydrous conditions and then adding mechlorethamine hydrochloride to produce a heterogenous mixture that is heated and stirred; and (b) adding water to the heterogeneous mixture and extracting with ethyl acetate to produce 1-(N-chloroethyl-N-methylaminoethoxy)-4-hydroxythioxanthone.

21. The compound 1-(N,N-bischloroethylaminoethoxy)-4-tert-butyldimethylsilyloxythioxanthone.

22. A method of selectively delivering a cytotoxic compound to tumor tissue, such method comprising administering to a mammal a proto-drug of the Formula I Formula I

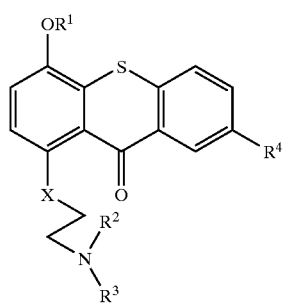

wherein:

$R^1$ is $SiZ_3$;

$R^2$ is methyl, chloroethyl, hydroxyethyl, or bromoethyl;

$R^3$ is chloroethyl, hydroxyethyl, or bromomethyl;

$R^4$ is H, $SO_3H$, or taurine;

each Z of $Z_3$ is independently methyl or t-butyl; and

X is carbon, oxygen, or nitrogen whereby the proto-drug delivers a cytotoxic compound to the tumor tissue in such a manner as to prevent significant damage to normal tissues by maintaining the cap moiety on the proto-drug until the proto-drug differentially concentrates in the tumor tissue during a time delay, and after such time delay the proto-drug is converted into the cytotoxic compound upon administration of an activation drug.

23. A method of selectively delivering a cytotoxic compound to tumor tissue, such method comprising administering to a mammal a proto-drug of the Formula II Formula II

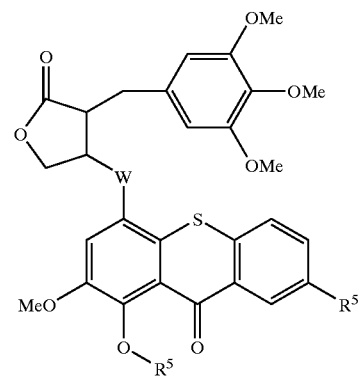

wherein:

$R^5$ is $SiZ_3$;

$R^6$ is H, $SO_3H$, or taurine;

each Z of $Z_3$ is independently methyl or t-butyl; and

W is carbon, oxygen, or nitrogen whereby the proto-drug delivers a cytotoxic compound to the tumor tissue in such a manner as to prevent significant damage to normal tissues by maintaining the cap moiety on the proto-drug until the proto-drug differentially concentrates in the tumor tissue during a time delay, and after such time delay the proto-drug is converted into the cytotoxic compound upon administration of an activation drug.

* * * * *

UNITED STATES PATENT AND TRADEMARK OFFICE
CERTIFICATE OF CORRECTION

PATENT NO. : 6,767,919 B2  Page 1 of 2
DATED : July 27, 2004
INVENTOR(S) : Evan Harris Walker et al.

It is certified that error appears in the above-identified patent and that said Letters Patent is hereby corrected as shown below:

Column 25,
Line 25, change Formula IV " 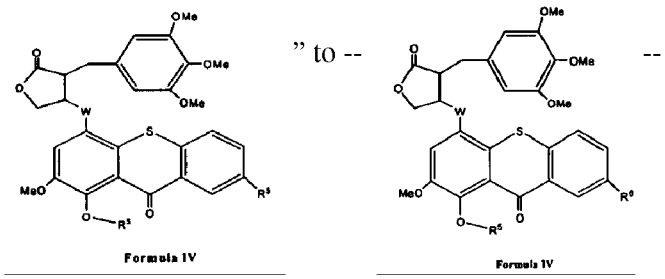 " to -- --

Column 26,
Line 20, change "Formula II " 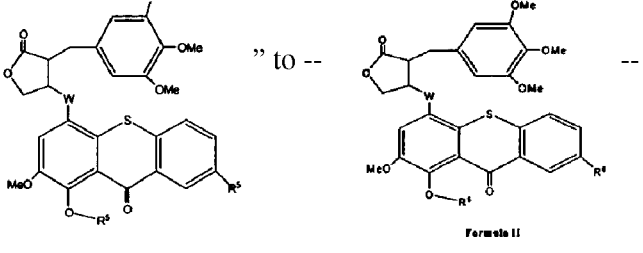 " to -- --

Column 27,
Line 10, change Formula IV " 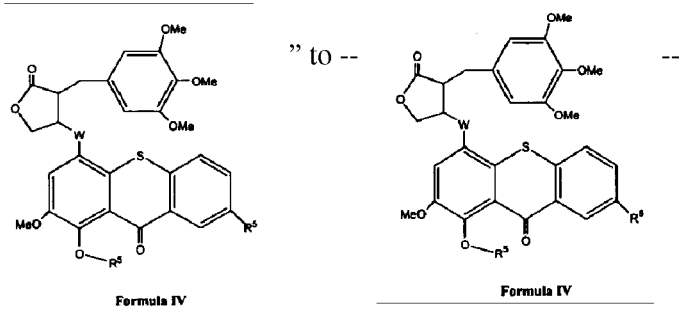 " to -- --

Column 30,
Line 25, change Formula II " 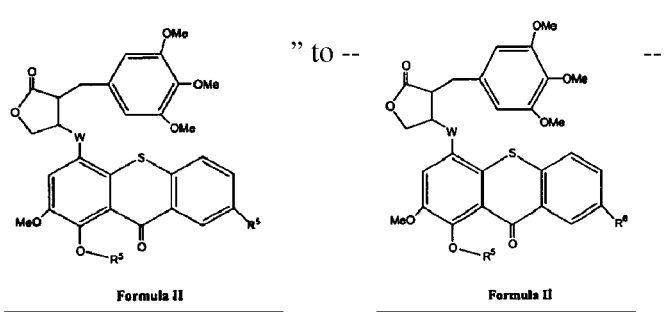 " to -- --

UNITED STATES PATENT AND TRADEMARK OFFICE
CERTIFICATE OF CORRECTION

PATENT NO. : 6,767,919 B2
DATED : July 27, 2004
INVENTOR(S) : Evan Harris Walker et al.

It is certified that error appears in the above-identified patent and that said Letters Patent is hereby corrected as shown below:

Column 28,
Line 3, change Formula II " 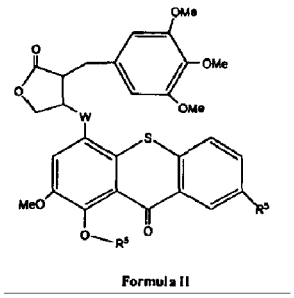 " to -- 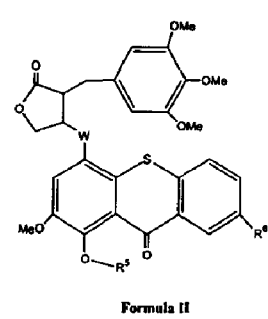 --

Signed and Sealed this

Fifteenth Day of March, 2005

JON W. DUDAS
*Director of the United States Patent and Trademark Office*